(12) United States Patent
Fujita et al.

(10) Patent No.: US 6,706,746 B2
(45) Date of Patent: Mar. 16, 2004

(54) THIAZOLIDINE-2,4-DIONE HYDROCHLORIDE SALT, PHARMACEUTICAL COMPOSITIONS THEREOF AND TREATMENT METHOD THEREWITH

(75) Inventors: Takashi Fujita, Kashiwa (JP); Toshihiko Fujiwara, Ebina (JP); Takashi Izumi, Yokohama (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/991,100

(22) Filed: Nov. 21, 2001

(65) Prior Publication Data

US 2002/0111373 A1 Aug. 15, 2002

Related U.S. Application Data

(63) Continuation of application No. PCT/JP00/03325, filed on May 24, 2000.

(30) Foreign Application Priority Data

May 24, 1999 (JP) ............................................. 11-143513

(51) Int. Cl.[7] ...................... A61K 31/427; C07D 417/12
(52) U.S. Cl. ........................................ 514/369; 548/181
(58) Field of Search ........................... 518/181; 514/369

(56) References Cited

U.S. PATENT DOCUMENTS

| 5,886,014 A | 3/1999 | Fujita et al. |
| 6,159,997 A | 12/2000 | Tsujita et al. |

2002/0137776 A1 * 9/2002 Kurakata et al. ............ 514/364

FOREIGN PATENT DOCUMENTS

| EP | 0 745 600 A1 | 12/1996 |
| HU | P9601808 A | 4/1997 |
| JP | 9-295970 A | 11/1997 |

OTHER PUBLICATIONS

Berge et al., Journal of Pharmaceutical Sciences (Jan. 1977), vol. 66, No. 1, pp. 1–19.*

* cited by examiner

Primary Examiner—Laura L. Stockton
(74) Attorney, Agent, or Firm—Frishauf, Holtz, Goodman & Chick, P.C.

(57) ABSTRACT

The present invention concerns the hydrochloride of the compound (5-[4-(6-methoxy-1-methyl-1H-benzimidazol-2-ylmethoxy)benzyl]thiazolidin-2,4-dione) of the following structure (I) which exhibits an excellent hypoglycemic activity and the like.

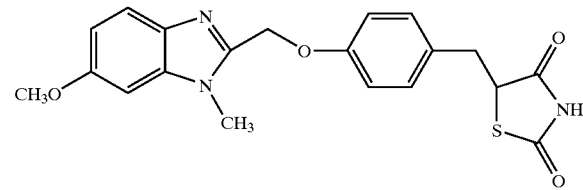

(I)

Said hydrochloride is useful when administered to patients for the treatment and/or prophylaxis of diabetes mellitus, hyperglycemia, impaired glucose tolerance and the like.

10 Claims, No Drawings

THIAZOLIDINE-2,4-DIONE HYDROCHLORIDE SALT, PHARMACEUTICAL COMPOSITIONS THEREOF AND TREATMENT METHOD THEREWITH

This application is a continuation application of International Application PCT/JP00/03325 (not published in English) filed May 24, 2000 which is incorporated herein by reference.

The present invention relates to the hydrochloride salt of a fused heterocyclic compound which can improve certain diseases caused by insulin resistance such as hyperglycemia, impaired glucose tolerance (IGT) conditions, diabetic complications (e.g., retinopathy, nephropathy, neurosis, cataracts, coronary artery diseases, etc.), hyperlipidemia, gestational diabetes mellitus (GDM), polycystic ovary syndrome, etc. and exhibits excellent oral absorption.

Further, this invention is directed to a prophylactic and therapeutic agent for diabetes mellitus, hyperglycemia, impaired glucose tolerance, diabetic complications (e.g., retinopathy, nephropathy, neurosis, cataracts, coronary artery diseases), hyperlipidemia, obesity, hypertension, fatty liver, arteriosclerosis, diseases caused by insulin resistance, gestational diabetes, polycystic ovary syndrome, cardiovascular diseases (e.g., ischemic heart disease), cell lesions caused by atherosclerosis or ischemic heart disease (e.g., brain damage induced by stroke), gout, inflammatory diseases (e.g., arthrosteitis, pain, fever, rheumatoid arthritis, inflammatory enteritis, acne, sunburn, psoriasis, eczema, allergic diseases, asthma, GI ulcer, cachexia, autoimmune diseases, pancreatitis), cancer, osteoporosis, cataracts and the like, which contains said fused heterocyclic compound hydrochloride as an active ingredient.

Furthermore, the present invention concerns a fused heterocyclic compound hydrochloride showing excellent insulin tolerance improving activity, hypoglycemic activity, anti-inflammatory activity, immunoregulatory activity, aldose reductase inhibiting activity, 5-lipoxygenase inhibiting activity, peroxidized lipid production suppressing activity, PPAR activating activity, anti-osteoporosis activity, leukotrienes antagonistic activity, fat cell formation promoting activity, cancer cell proliferation suppressing activity and calcium antagonistic activity.

BACKGROUND OF THE INVENTION

Insulin and sulfonylurea compounds such as tolbutamide, glipizide, etc. have been used as therapeutic agents for diabetes mellitus and hyperglycemia. Recently, as insulin-independent therapeutic agents for diabetes mellitus, there are known thiazolidinedione derivatives such as troglitazone, pioglitazone, rosiglitazone, etc.

In particular, 5-[4-(6-methoxy-1-methyl-1H-benzimidazol-2-ylmethoxy)benzyl]thiazolidin-2,4-dione is disclosed in Japanese Patent Application Publication No. Hei-9(1997)-295970, EP 0745600, and U.S. Pat. No. 5,886,014. However, neither biological data nor physical properties of its hydrochloride, which is the compound of this invention, are disclosed in these documents.

SUMMARY OF THE INVENTION

As the result of keen investigations on the synthesis and pharmacology of compounds capable of improving the diseases caused by insulin resistance such as hyperglycemia, impaired glucose tolerance conditions, diabetic complications, hyperlipidemia, gestational diabetes, polycystic ovary syndrome, etc., the present inventors have found that the hydrochloride of a known fused heterocyclic compound shows excellent pharmacological activities.

Accordingly, the novel hydrochloride of a fused heterocyclic compound was obtained by converting a known compound, 5-[4-(6-methoxy-1-methyl-1H-benzimidazol-2-ylmethoxy)benzyl]thiazolidin-2,4-dione into its hydrochloride. This shows excellent oral absorption with markedly improved solubility compared to its free compound (compound not in the form of its salt). It can provide excellent pharmacological activities, because this excellent oral absorption will give the required serum concentration at a lower dosage.

The present invention concerns 5-[4-(6-methoxy-1-methyl-1H-benzimidazol-2-ylmethoxy)benzyl]thiazolidin-2,4-dione hydrochloride (hereinafter referred to as "Compound A").

Further, this invention is directed to a prophylactic and/or therapeutic agent for diabetes mellitus, hyperglycemia, impaired glucose tolerance, diabetic complications (e.g., retinopathy, nephropathy, neuropathy, cataracts, coronary artery diseases), hyperlipidemia, obesity, hypertension, fatty liver, arteriosclerosis, diseases caused by insulin resistance, gestational diabetes, polycystic ovary syndrome, cardiovascular diseases (e.g., ischemic heart disease), cell lesions (injury) caused by atherosclerosis or ischemic heart disease (e.g., brain damage induced by stroke), gout, inflammatory diseases (e.g., arthrosteitis, pain, fever, rheumatoid arthritis, inflammatory enteritis, acne, sunburn, psoriasis, eczema, allergic diseases, asthma, GI ulcer, cachexia, autoimmune disease, pancreatitis), cancer, osteoporosis, cataracts and the like containing, as an active ingredient, said Compound A.

The present invention also provides a method of treatment and/or prophylaxis by administering to a human or other mammal in need thereof, an active agent selected from an insulin resistance improving agent, hypoglycemic agent, anti-inflammatory agent, immuno-regulator, aldose reductase inhibitor, 5-lipoxygenase inhibitor, peroxidized lipid production suppressor, PPAR activator, anti-osteoporosis agent, leukotrienes antagonist, fat cell formation promotor, cancer cell proliferation suppressor or calcium antagonist containing Compound A as an active ingredient.

5-[4-(6-methoxy-1-methyl-1H-benzimidazol-2-ylmethoxy)benzyl]-thiazolidin-2,4-dione (hereinafter referred to as "Compound B"), the free form of Compound A of the present invention, is shown by the structural formula (I):

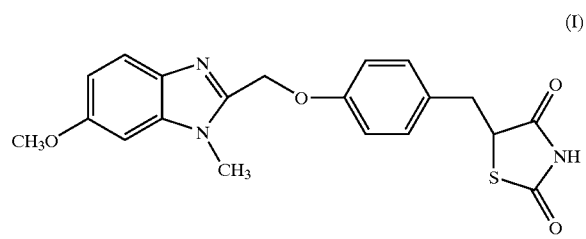

(I)

Moreover, said Compound A has various isomers. For example, there are optical isomers, depending upon the asymmetry of the 5-carbon atom of the thiazolidine ring. In said structure (I), all the stereoisomers based on these asymmetric carbon atoms as well as the isomeric mixtures in equal amounts or non-equal amounts are shown by a single structure. Thus, all these isomers and their mixtures are included in the present invention.

Furthermore, solvation of said Compound A may occur by allowing it to recrystallize, and such a solvate of the compound A will be covered by the present invention.

The Compound A in the present invention can be prepared by at first synthesizing Compound B according to Example (1) described below and then converting it into the hydrochloride as shown in Example (2) in a conventional manner.

Compound A in the present invention is useful as a prophylactic and/or therapeutic agent for administration to mammals, e.g. humans, for prevention and/or treatment of diabetes mellitus, hyperglycemia, impaired glucose tolerance, diabetic complications (e.g., retinopathy, nephropathy, neurosis, cataracts, coronary artery diseases), hyperlipidemia, obesity, hypertension, fatty liver, arteriosclerosis, diseases caused by insulin resistance, gestational diabetes, polycystic ovary syndrome, cardiovascular diseases (e.g., ischemic heart disease), cell lesions caused by atherosclerosis or ischemic heart disease (e.g., brain damage induced by stroke), gout, inflammatory diseases (e.g., arthrosteitis, pain, fever, rheumatoid arthritis, inflammatory enteritis, acne, sunburn, psoriasis, eczema, allergic diseases, asthma, GI ulcer, cachexia, autoimmune disease, pancreatitis), cancer, osteoporosis, cataracts and the like.

Compound A in the present invention is administered in the methods of the present invention, for example, by the oral route in such a formulation as tablets, capsules, granules, powders or syrups, or by the parenteral route in such a formulation as injections, suppositories or eye-drops. These formulations may be prepared employing well-known methods by using conventional carriers such as excipients, lubricants, binders, disintegrators, stabilizers, corrigents, diluents and the like.

As for the excipients, there are exemplified organic excipients, for example, sugar derivatives such as lactose, sucrose, glucose, mannitol and sorbitol; starch derivatives such as corn starch, potato starch, α-starch, dextrin and carboxymethyl starch; cellulose derivatives such as crystalline cellulose, low substituted hydroxypropyl cellulose, hydroxypropylmethyl cellulose, carboxymethyl cellulose, calcium carboxymethyl cellulose and sodium internal cross-linked carboxymethyl cellulose; arabic gum; dextran; pullulan; and inorganic excipients, for example, silicate derivatives such as light silicic anhydride, synthetic aluminum silicate and magnesium aluminate metasilicate; phosphates such as calcium phosphate; carbonates such as calcium carbonate; and sulfates such as calcium sulfate.

As for the lubricant, there are exemplified stearic acid, metal stearates such as calcium stearate and magnesium stearate; talc; colloidal silica; wax such as beeswax and spermaceti; boric acid; adipic acid; sulfates such as sodium sulfate; glycol; fumaric acid; sodium benzoate; DL-leucine; fatty acid sodium salts; lauryl sulfates such as sodium lauryl sulfate and magnesium lauryl sulfate; silicic acids such as silicic anhydride and silicic acid hydrate; and said starch derivatives.

Examples of the binder are polyvinylpyrrolidone, macrogol and those exemplified as said excipient.

Examples of the disintegrator are those exemplified as said excipient, and chemically modified starches and celluloses such as sodium cross-carmellose, sodium carboxymethyl starch and cross-linked polyvinylpyrrolidone.

Examples of the stabilizer are p-oxybenzoic acid esters such as methylparaben and propylparaben; alcohol derivatives such as chlorobutanol, benzyl alcohol and phenylethyl alcohol; phenol derivatives such as phenol and cresol; thimerosal; dehydroacetic acid; and sorbic acid.

Examples of the corrigents are those sweetening agents, souring agents, flavor agents, and the like used conventionally.

The appropriate daily dosage of Compound A in the present invention for a human adult varies depending upon symptoms, age, route of administration and the like. In the case of the oral route the daily dosage is, for example, from 0.01 mg/kg (of the body weight of the human adult) to 2000 mg/kg, and preferably 0.1 mg/kg to 500 mg/kg, and more preferably 0.1 mg/kg to 100 mg/kg in a single dose or in several divided doses in accordance with the symptoms. In the case of intravenous administration, the daily dosage of compound A for a human adult varies from 0.001 mg/kg to 500 mg/kg and preferably 0.01 mg/kg to 50 mg/kg which is preferably administered in a single dose or in several divided doses in accordance with the symptoms of the patient. Dosage for a specific patient is determined by those skilled in the art by applying usual techniques.

EXAMPLES

5-[4-(6-Methoxy-1-methyl-1H-benzimidazol-2-ylmethoxy)benzyl]thiazolidin-2,4-dione hydrochloride (1) 5-[4-(6-Methoxy-1-methyl-1H-benzimidazol-2-ylmethoxy)benzyl]thiazolidin-2,4-dione (Compound B)

A mixture of 21.8 g of 5-methoxy-N-methyl-1,2-phenylenediamine (see Referential Example 9, Japanese Patent Application Publication No. Hei-9 (1997)-295970), 63.4 g of 5-(4-methoxycarbonylmethoxybenzyl)thiazolidin-2,4-dione (see Referential Example 21, Japanese Patent Application Publication No. Hei9-(1997)-295970), 250 ml of 1,4-dioxane and 750 ml of conc. hydrochloric acid was heated under reflux for 60 hours. The reaction mixture was cooled with ice, and the precipitate was filtered. The precipitate was mixed with 800 ml of 5% aqueous sodium hydrogencarbonate solution and stirred at room temperature for 2 hours. The insoluble material was filtered, dissolved in a mixture of 1000 ml of N,N-dimethylformamide and 200 ml of methanol and treated with activated charcoal. The activated charcoal was filtered off, and the filtrate was concentrated to about 50 ml by evaporating the solvents. To the residue was added 750 ml of diethyl ether and this was then allowed to stand at room temperature for 2 days. The precipitate was filtered to give 20.1 g of the desired compound having a melting point of 267–271° C. having an Rf=0.68 (thin layer chromatography on silica gel; 5% ethanol-methylene chloride solution).

(2) 5-[4-(6-Methoxy-1-methyl-1H-benzimidazol-2-ylmethoxy)benzyl]thiazolidin-2,4-dione Hydrochloride (Compound A)

A mixture of 10.6 g of 5-[4-(6-methoxy-1-methyl-1H-benzimidazol-2-ylmethoxy)benzyl]thiazolidin-2,4-dione (Compound B) obtained in (1) and 100 ml of 4N hydrochloric acid-1,4-dioxane was stirred at room temperature for 1 hour. The reaction mixture was concentrated and mixed with ethyl acetate. The precipitated product was filtered and washed with ethyl acetate to give 11.0 g of the title compound (i.e., the monohydrochloride) having a melting point of 275–277° C.

$^1$H-NMR Spectrum $^1$H-NMR spectrum (400 MHz) measured in deuterated dimethyl sulfoxide by using TMS (tetramethylsilane) as an internal standard: δ(ppm): 3.11 (1H, dd, J=14Hz and 9Hz), 3.34 (1H, dd, J=14Hz and 4 Hz), 3.89 (3H, s), 3.98 (3H, s), 4.91 (1H, dd, J=9Hz and 4 Hz), 5.64 (2H, s), 7.14 (2H, d, J=9Hz), 7.15 (1H, d, J=9Hz), 7.25 (2H, d, J=9Hz), 7.50 (1H, s), 7.70 (1H, d, 9Hz), 12.04 (1H, s, disappeared by adding D$_2$O)

Biological Test Experiment

Male spontaneously diabetic rats (ZDF/Gmi-fa/fa) which were 8–10 weeks old were used.

The test compound was suspended in 0.5% CMC solution, and a dose of 0.33 mg/ml/kg was orally administered consecutively for 2 weeks under compulsion. The blood sugar level was measured in a conventional manner. Thus, the tail end (about 1 mm) of rat was cut, and the blood was collected with a hematocrit tube treated with heparin for anti-coagulation and centrifuged. The resultant plasma was measured with Glucoloader F (A&T).

Table 1 shows the results of the blood sugar lowering activity test on Compound A (this invention), a non-treated group and Compound B. Further, all the values of Table 1 mean average value of the test result using 6 spontaneously diabetic male rats (ZDF/Gmi-fa/fa).

TABLE 1

| | Blood Sugar Level (mg/dl) | | | |
|---|---|---|---|---|
| | 0 Hour | 3 Days | 7 Days | 14 Days |
| Non-treated Group | 456 | 495 | 576 | 590 |
| Compound B | 456 | 379 | 409 | 535 |
| Compound A | 456 | 228 | 206 | 207 |

It was evident from the result of Table 1 that Compound A of the present invention showed a more excellent hypoglycemic activity than Compound B, its free form.

Further, on the contrary the blood sugar level in the non-treated group increased with the lapse of time.

Solubility Experiment

To 200 ml of the $1^{st}$ fluid of Japanese Pharmacopeia (1000 ml solution made by mixing 2.0 g of sodium chloride with 7.0 ml of hydrochloric acid and water) were added 40 mg of Compound A or Compound B, and the mixture was stirred with a stirrer at 37° C. in a 300 ml conical beaker. One hour later, 10 ml of the sample were filtered through Acrodisk LC13 (PVDF, manufactured by German Science Co.). The initial 3 ml were discarded, and the following 7 ml were taken into a test tube. Of this sample, 5 ml were taken accurately with a whole pipette and added to 2 ml of methanol accurately measured in advance in a test tube.

The quantity was measured by HPLC and the solubility was decided from a calibration curve made according to the following procedure.

The calibration curve was made by preparing a methanolic standard solution of Compound A at a concentration of 400 µg/ml, 100 µg/ml and 20 µg/ml, mixing each 2 ml of the standard solution with 5 ml of the $1^{st}$ fluid of Japanese Pharmacopeia and determined by HPLC.

HPLC Condition

Analytical column: L-column ODS (4.6 mm ID×15 cm, manufactured by Chemicals Evaluation Research Institute Japan)
Mobile phase: 0.01 mol/L acetic acid buffer solution (pH 5.0)/acetonitrile mixture (13:7)
Flow rate: about 1.0 ml/min.
Column temperature: 40° C.
Detector: ultraviolet absorptiometer (measuring wavelength: 290 nm)

TABLE 2

Table 2 shows the result.

| | 0 Hour | Solubility 1.0 hour later (µg/mL) |
|---|---|---|
| Compound B | 0.0 | 41.0 |
| Compound A | 0.0 | 86.4 |

It is evident from the result of Table 2 that Compound A prepared by converting Compound B into its hydrochloride shows a markedly better solubility than Compound B.

Formulation Example

Formulations containing Compound A of the present invention as an active ingredient can be prepared, for example, according to the following methods.

Formulation 1. Powder

A powder is prepared by pulverizing a mixture of 4 g of Compound A of the present invention, 10 g of polyvinylpyrrolidone and 0.5 g of hydroxypropylmethyl cellulose (trade mark TC-5E manufactured by Shin-Etsu Chemical Co., Ltd.) in a vibration mill for 30 minutes.

Formulation 2. Capsule

In a mixture of 100 g of acetone and 100 g of ethanol are dissolved 20 g of Compound A and 20 g of polyvinylpyrrolidone, and the solution is sprayed over 200 g of sodium cross-carmellose using a fluidized bed granulator to give granules. The granules (10 g) are mixed with 0.1 g of hydroxypropylmethyl cellulose (trade-mark TC-5E manufactured by Shin-Etsu Chemical Co., Ltd.) and 1.9 g of lactose. Then, 0.24 g of the mixture are charged in a gelatin capsule to give the capsule. This capsule contains 0.1 g of Compound A.

Formulation 3. Tablet 1 g of Compound A and 1 g of polyvinylpyrrolidone are dissolved in a mixture of 5 g of acetone and 5 g of ethanol, and the solution is concentrated in vacuo with a rotary evaporator to remove the organic solvents. The solid thus-obtained is pulverized to give fine granules. To 1 g of the fine granules are added 0.25 g of crystalline cellulose, 0.25 g of low substituted hydroxypropyl cellulose, 0.05 g of hydroxypropylmethyl cellulose (trade mark TC-5E, manufactured by Shin-Etsu Chemical Co., Ltd.), 0.18 g of lactose and 0.2 g of magnesium stearate, and the mixture is tableted by a tabulet machine to give tablets.

The present compound, 5-[4-(6-methoxy-1-methyl-1H-benzimidazol-2-ylmethoxy)benzyl]thiazolidin-2,4-dione hydrochloride shows excellent insulin tolerance improving activity, hypoglycemic activity, anti-inflammatory activity, immunoregulatory activity, aldose reductase inhibiting activity, 5-lipoxygenase inhibiting activity, peroxidized lipid production suppressing activity, PPAR activating activity, anti-osteoporosis activity, leukotrienes antagonistic activity, fat cell formation promoting activity, cancer cell proliferation suppressing activity and calcium antagonistic activity.

Accordingly, the compound of the present invention is useful for treatment and/or prophylaxis of diabetes mellitus, hyperglycemia, impaired glucose tolerance, diabetic complications (e.g., retinopathy, nephropathy, neurosis, cataracts, coronary artery diseases), hyperlipidemia, obesity, hypertension, fatty liver, arteriosclerosis, diseases caused by insulin resistance, gestational diabetes, polycystic ovary syndrome, cardiovascular diseases (e.g., ischemic heart disease), cell lesions caused by atherosclerosis or ischemic heart disease (e.g., brain damage induced by stroke), gout, inflammatory diseases (e.g., arthrosteitis, pain, fever, rheumatoid arthritis, inflammatory enteritis, acne, sunburn, psoriasis, eczema, allergic diseases, asthma, GI ulcer, cachexia, autoimmune diseases, pancreatitis), cancer, osteoporosis, cataracts and the like.

What is claimed is:

1. 5-[4-(6-Methoxy-1-methyl-H-benzimidazole-2-ylmethoxy)benzyl]-thiazolidin-2,4-dione hydrochloride.

2. A pharmaceutical composition comprising an effective amount of the compound of claim 1 together with a carrier therefor.

3. A method of treatment or prophylaxis of a human having a disease selected from the group consisting of diabetes mellitus, hyperglycemia, impaired glucose tolerance, diabetic complications, hyperlipidemia, obesity, hypertension, fatty liver, arteriosclerosis, gestational diabetes, polycystic ovary syndrome, cardiovascular diseases, atherosclerosis, and inflammatory diseases, comprising administering to said human an effective amount of the compound of claim 1.

4. A method according to claim 3 wherein said disease is diabetes mellitus.

5. A method according to claim 3 wherein said disease is impaired glucose tolerance.

6. A method according to claim 3 wherein said disease is diabetic complications.

7. A method of treating a mammal in need of treatment and having a disease selected from the group consisting of diabetes mellitus, hyperglycemia, impaired glucose tolerance, diabetic complications, hyperlipidemia, obesity, hypertension, fatty liver, arteriosclerosis, gestational diabetes, polycystic ovary syndrome, cardiovascular diseases, atherosclerosis, and inflammatory diseases, comprising administering to said mammal an effective amount of the compound of claim 1.

8. A method of treating a mammal in need of treatment according to claim 7 wherein said disease is diabetes mellitus.

9. A method of treating a mammal in need of treatment according to claim 7 wherein said disease is impaired glucose tolerance.

10. A method of treating a mammal in need of treatment according to claim 7 wherein said disease is diabetic complications.

* * * * *